(12) United States Patent
Shishihara et al.

(10) Patent No.: US 6,389,907 B2
(45) Date of Patent: May 21, 2002

(54) O-RING TEST DEVICE

(75) Inventors: Yo Shishihara, Ina; Kunihiko Takagi, Nagano-ken; Takeshi Seto, Chofu; Satoshi Kinoshita, Matsumoto; Yoshinori Awanohara, Minamiminowa-mura, all of (JP)

(73) Assignee: Seiko Epson Corporation (JP)

( * ) Notice: Subject to any disclaimer, the term of this patent is extended or adjusted under 35 U.S.C. 154(b) by 0 days.

(21) Appl. No.: 09/841,470

(22) Filed: Apr. 24, 2001

(30) Foreign Application Priority Data

Apr. 28, 2000 (JP) .................................... 2000-129935

(51) Int. Cl.[7] ................................................ G01N 1/00
(52) U.S. Cl. ........................................ 73/849; 73/826
(58) Field of Search .................... 73/818, 826, 828, 73/831, 833, 835, 836, 837, 849

(56) References Cited

U.S. PATENT DOCUMENTS 5,913,835 A * 6/1999 Naoi et al. .................. 600/595

FOREIGN PATENT DOCUMENTS

| JP | 02136136 A | 5/1990 |
| JP | 07-155314 | 6/1995 |
| JP | 07-163552 | 6/1995 |
| JP | 08-024246 | 1/1996 |
| JP | 08-038463 | 2/1996 |

* cited by examiner

*Primary Examiner*—Max Noori
(74) *Attorney, Agent, or Firm*—Harness, Dickey & Pierce, P.L.C.

(57) ABSTRACT

The present device, generates external force tending to open the O-ring formed by the thumb and another finger of the examiner and composed of a pair of artificial finger sections including two artificial fingers 8A and 8B. The artificial fingers 8A and 8B include two slender tubes 12 and 14 having corrugated wall faces, core members 16 for maintaining the parallel arrangement of the tubes 12 and 14, and thin bag-like covering members 18 consisting of a high polymer for covering the outer periphery of the tubes 12 and 14. Pump sections 10 for controlling movement of low viscosity hydraulic oil serving as a fluid sealed in fluid chambers 12a and 14a are integrally connected to base ends of the artificial fingers 8A and 8B.

17 Claims, 4 Drawing Sheets

O-RING TEST DEVICE

BACKGROUND OF THE INVENTION

1. Technical Field of the Invention

The present invention relates to an O-ring test device for measuring various human body information, such as a body-compatibility determination, an abnormal area determination, and information identification.

2. Description of the Related Art

Hitherto, in medical diagnosis, a technique called "a bi-digital O-ring test" (hereinafter, referred to as "an O-ring test") has been known as a method for diagnosing an abnormal area of an examinee (patient) (U.S. Pat. No. 5,188,107). In this test, one finger satisfying the condition of being one of the second, third, fourth, and fifth fingers is placed against the first finger (thumb) of one hand of the examinee, a ring (O-ring) is formed by the two fingers, and the examinee is allowed to apply force to the fingers continuously. An examiner (measurer) opens the two fingers from both sides with examiner's fingers. The strength of the fingers of the examinee tending to maintain the two fingers as they are against the examiner is determined.

This O-ring test is a living body sensor test making use of the muscular tonus condition. If the muscle strength of the fingers becomes weakened in a state where an arbitrary organ representation point is pointed to by the examinee, the O-ring opens. This means that the organ is abnormal. Conversely, when the O-ring is strong enough not to open, this means that the organ is normal. Incidentally, the meaning of the above is reversed only in the case of the thymus gland. This can find the abnormal areas of the body.

In addition, if the same technique is performed by having a sample of a particular material in the examinee's hand, the muscle strength of the fingers of the examinee will become weakened and the O-ring will open if the same material in the examinee's hand exists inside the body of the examinee. When the material exists, the muscle strength of the fingers becomes weakened and the O-ring opens. This has been interpreted to be a phenomenon resulting from the resonance of the substances, and is called a resonance test. By making use of this method, the distribution of bacteria, viruses, cancer, metabolic substances in a living body, hormones, nerve transmission substances, heavy metals, drugs, and the like in the living body can be determined, and diseases can be diagnosed. Incidentally, this O-ring test is an auxiliary diagnostic method that is conducted before the diagnosis made by using the latest normal medical equipment.

Incidentally, in the above-described O-ring test, there is a possibility that uncertain factors will enter into the fingers of the examiner tending to open the O-ring. That is, although the examiner must produce external force for opening the O-ring with a fixed power and the same rhythm every time, the examiner may conduct the O-ring test with non-uniform force. In addition, even if the examiner has the intention of applying the force uniformly to the fingers, since there is no objective indicator, effects due to suggestion or other conscious effects may appear.

Thus, as a device for conducting the O-ring test by an object other than the fingers of the examiner, devices disclosed in Japanese Unexamined Patent Application Publication No. 07-163552 (hereinafter, referred to as a first conventional art) and in Japanese Unexamined Patent Application Publication No. 08-38463 (hereinafter, referred to as a second conventional art) have been known.

The first conventional art discloses a device in which a bag means is inserted in an O-ring formed by the thumb and another finger of an examinee, the bag means is expanded by a control of injecting means to generate external force tending to open the O-ring, and then contact-separation state of the fingers forming the O-ring is detected by contact-separation detecting means based on the inflow and outflow state of gas, and a change in muscle strength of voluntary muscles before and after the detection of the separation of the fingers (the thumb and another finger) is secondarily measured based on the output of pressure detecting means.

The second conventional art discloses a device in which a pair of rings are engaged with the thumb and another finger of the examinee forming the O-ring, external force tending to open the O-ring is generated on the pair of rings by the power of an electric motor, the external force is measured based on the output of the external force detecting means, and the measurement result of the external force given to the thumb and another finger just before the detection of the separation of the thumb and another finger measured for the examinee before the O-ring test are comparatively operated by measuring means.

Since the external force for opening the O-ring is imparted by the bag means in the first conventional art and by the pair of rings in the second conventional art instead of the fingers of the examiner (measurer) into which uncertain factors enter, these conventional arts can impart fixed external force to the O-ring.

In the first conventional art, however, since the gas is injected to the bag means inserted in the O-ring so as to open the O-ring by the expansion of the bag means, unlike an original O-ring test for opening two fingers of the O-ring by the fingers of the examiner, the function of the O-ring test may not be sufficiently exhibited.

In addition, in the second conventional art, since the pair of rings locally come into contact with the thumb and another finger of the examinee forming the O-ring and do not come into contact softly, unlike human fingers, an uncomfortable sensation is given to the examinee. In addition, since the electric motor is used in the conventional art, electromagnetic waves generated by the electric motor exerts an influence on the vital reaction, whereby the result of the O-ring test may not be obtained accurately, and the device may be a large test device.

The present invention has been achieved in consideration of the above circumstances, and an object is to provide a compact O-ring test device which softly contacts the thumb and another finger of an examinee forming the O-ring like human fingers to generate external force in a direction to open the O-ring, and which can obtain the results of an O-ring test by preventing the influence of the device on a vital reaction.

SUMMARY OF THE INVENTION

In order to solve the above problems, there is provided an O-ring test device for forming an O-ring by a thumb and another finger consisting of voluntary muscles of an examinee, and for measuring body information according to a change in muscle strength of the voluntary muscles with external force tending to open the O-ring opposed against the muscle strength of the voluntary muscles of the examinee, the O-ring test device including: at least two artificial fingers engaging with the thumb and another finger forming the O-ring, having at least two fluid-sealed fluid chambers arranged parallel to each other, and generating the external force tending to open the O-ring by being bent and deformed by the movement of the fluid between the fluid chambers; pump means for moving the fluid between the plurality of fluid chambers; pressure detecting means for detecting pressure values in the artificial fingers when the external force is being generated; pump driving means for controlling the drive of the pump means; contact-separation detecting means for detecting contact and separation of the thumb and another finger; and a muscle strength change-calculating means for calculating a change in muscle strength of the voluntary muscles before and after the separation of the thumb and another finger detected by the contact-separation detecting means based on the output of the pressure detecting means.

In addition, there is provided an O-ring test device further including display means for displaying the result of the muscle strength change-calculating means.

In addition, there is provided an O-ring test device wherein the pump means is integrally connected to the base ends of the artificial fingers.

In addition, there is provided an O-ring test device wherein the pump means includes a diaphragm defining a pump fluid chamber between the pump means and ends of the artificial fingers; a piezoelectric element stacked on the diaphragm; and a valve part for setting a direction of movement of the fluid between the fluid chamber of one tube and the fluid chamber of the other tube.

In addition, there is provided an O-ring test device wherein the artificial fingers have a construction in which at least two slender tubes capable of expansion and contraction and having a fluid chamber accommodating therein a fluid are arranged in parallel to each other, and a flexible core member for controlling the lengthwise expansion of the tubes is provided between the tubes.

In addition, there is provided an O-ring test device wherein the tubes of the artificial fingers contacting the thumb and another finger forming the O-ring are formed of flexible elastic materials.

Furthermore, there is provided an O-ring test device wherein the fluid sealed in the fluid chambers is liquid, and the outer periphery of the artificial fingers is covered by an outer periphery-covering member having a liquid absorption function.

DETAILED DESCRIPTION OF THE PREFERRED EMBODIMENTS

The embodiment of an O-ring test device according to the present invention will be described below with reference to the drawings.

Figure 1:
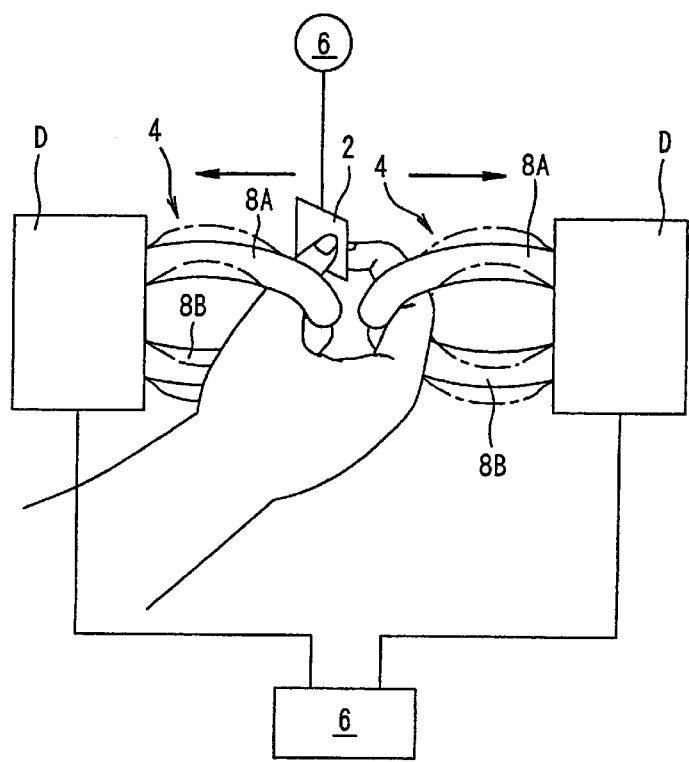
FIG. 1 is a view showing the general configuration of an O-ring test device according to the present invention.

FIG. 1 shows an O-ring test device of a first embodiment. The device includes a contact-separation detecting sensor 2 clipped to tips of a thumb and another finger of an examinee forming an O-ring, a pair of artificial finger sections 4, each base end thereof being supported on a fixed section D made of soft rubber so as to generate external force tending to open the O-ring, and a device body 6 for controlling the drive of the pair of artificial finger sections 4, and for calculating and displaying a change in muscle strength of voluntary muscles of the thumb and another finger when the external force is generated.

Figure 2:
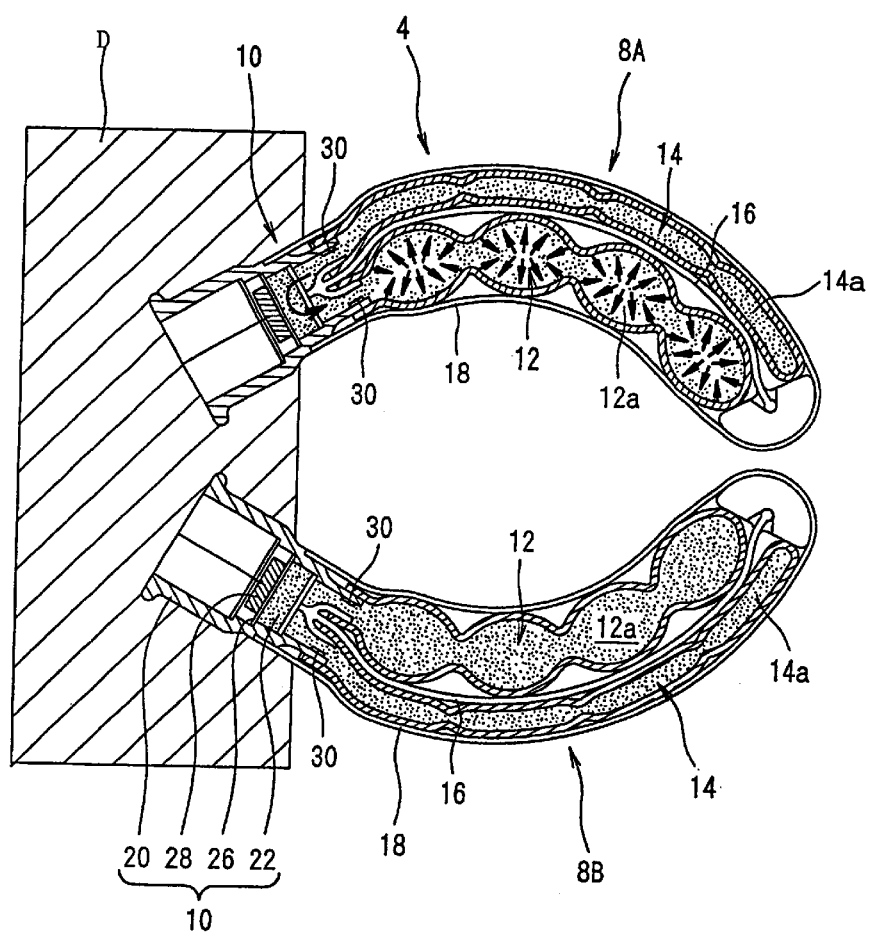
FIG. 2 is a view showing artificial fingers and pump means constituting the O-ring test device.

As shown in FIG. 2, artificial finger sections 4 include two artificial fingers 8A and 8B, and pump sections 10 which are integrally connected to base ends of the artificial fingers 8A and 8B, and which controls movement of low viscosity hydraulic oil serving as a fluid sealed in the artificial fingers 8A and 8B.

The artificial fingers 8A and 8B include two slender tubes 12 and 14 having corrugated wall faces, core members 16 for maintaining the parallel arrangement of the tubes 12 and 14, and thin bag-like covering members 18 consisting of a high polymer for covering the outer periphery of the tubes 12 and 14.

The tubes 12 and 14 are formed of flexible elastic materials, and have fluid chambers 12a and 14a inside thereof to seal hydraulic oil, such as liquid silicone, therein. In addition, the core members 16 are, for example, flexible steel members, and allow the widthwise expansion of the tubes 12 and 14 while controlling the lengthwise expansion.

Each pump section 10 adopts a piezoelectric diaphragm pump, and includes a cylindrical pump section case 20 integrally connected to the lower part of the artificial fingers 8A and 8B while being maintained fluid-tight, an active valve 22 serving as a valve part provided in the pump section case 20 for partitioning the fluid chambers 12a and 14a of the tubes 12 and 14, a diaphragm 26 defining a pump fluid chamber (not shown) in a space under the active valve 22, and a piezoelectric element 28 stacked on the lower surface of the diaphragm 26.

The pump section case 20 is buried in the above-described fixed section D. In addition, the piezoelectric element 28 is a known piezoelectric actuator consisting of an element having a so-called piezoelectric effect. While there are various materials having the piezoelectric effect, ranging from crystals to high polymers, a typical material for the piezoelectric actuator is lead zirconate titanate (PZT), which is one of the piezoelectric ceramics. By changing a voltage applied to the piezoelectric element 28, the piezoelectric element 28 is extended, whereby the shape of the diaphragm 26 is changed to vary internal pressure of the pump fluid chamber.

Although it is not shown in the figure, the active valve 22 is a device including, for example, a solenoid-type switching valve for setting a direction of movement of the hydraulic oil between the two fluid chambers, and is operated by an open-close controlling current transmitted from the device body 6.

Here, the tubes 12 and 14 are provided with pressure sensors 30 for detecting fluid pressure of the fluid chambers 12a and 14a, and detected information of the fluid pressure is transmitted to the device body 6 at any time.

Figure 3:
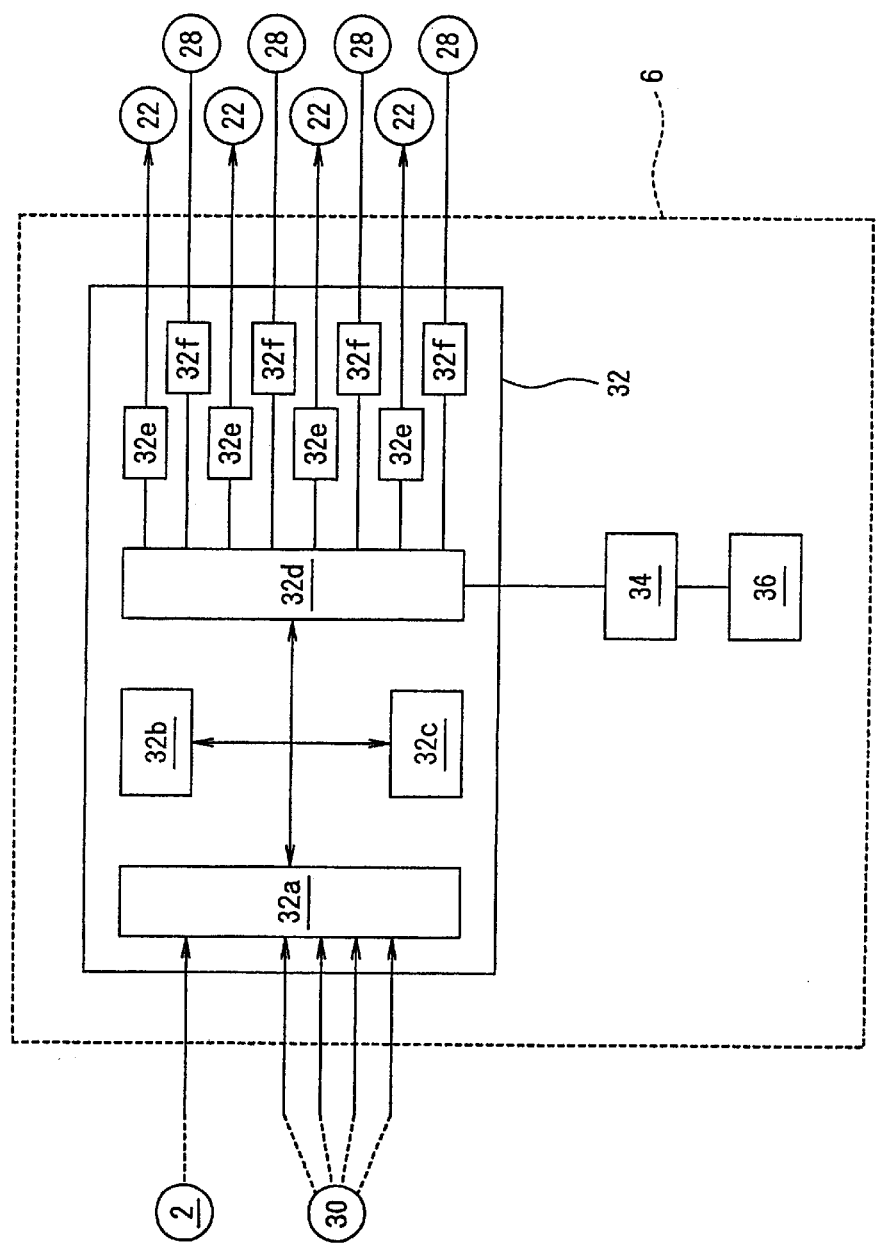
FIG. 3 is a view showing a device body of the O-ring test device.

On the other hand, the device body 6 includes a microcomputer 32, a driver 34, a display 36, and a control panel (not shown) as shown in FIG. 3.

The microcomputer 32 includes an input interface circuit 32a having the A/D converting function for reading detection signals from the contact-separation sensor 2 and a plurality of pressure sensors 30 as detection values, a processing unit 32b for performing a predetermined processing for controlling the drive of the pump sections 10 in accordance with a predetermined program and for calculating a change in muscle strength of voluntary muscles, a storage unit 32c, such as a RAM or a ROM, an output interface circuit 32d for outputting open-close controlling signals for the active valves 22 obtained by the processing unit 32b and voltage controlling signals for the piezoelectric elements 28, active valve driving circuits 32e for outputting open-close controlling current to the active valves 22 based on the open-close controlling signals output from the output interface circuit 32d, and terminal voltage controlling circuits 32f for outputting terminal voltages to the piezoelectric elements 28 based on the voltage controlling signals output from the output interface circuit 32d. Here, a pressure value of the fluid chamber 12a, which is changed when the O-ring test is started, and a storage table of the muscle strength of the voluntary muscles of the examiner forming the O-ring corresponding to the pressure value are stored in the storage device 32c.

In addition, display data is supplied to the driver 34 from the microcomputer 32, whereby the driver 34 drives the display 36 based on the display data, and displays the results of the O-ring test.

Next, the procedure for conducting the O-ring test, and operations of the members will be described briefly with reference to FIGS. 1 to 3.

First, it is assumed that an examinee forms an O-ring by the thumb and the forefinger, as shown in FIG. 1.

Next, the examiner operates the control panel to instruct the start of the O-ring test. This allows the microcomputer 32 to output open-close controlling signals from the active valve driving circuits 32e to control open and close of the active valves 22 for every predetermined time so that a communication state of the fluid chamber 12a and the pump fluid chamber and a communication state of the fluid chamber 14a and the pump fluid chamber are repeated. At the same time, when the fluid chamber 14a communicates with the pump fluid chamber, the piezoelectric elements 28 are extended by the terminal voltage output from the terminal voltage controlling circuits 32f, and the diaphragm 26 is elastically deformed downward to decrease the internal pressure of the pump fluid chamber to thereby allow the hydraulic oil in the fluid chamber 14a to flow into the pump fluid chamber. In addition, when the fluid chamber 12a communicates with the pump fluid chamber, output of the terminal voltage from the terminal voltage control circuits 32f is stopped, and the diaphragm 26 is elastically returned to the original state to increase the internal pressure of the pump fluid chamber to thereby allow the hydraulic oil in the pump fluid chamber to flow into the fluid chamber 12a. The pump sections 10 repeat these actions to move the hydraulic oil from the fluid chamber 14a of the tube 14, which is not in contact with the fingers forming the O-ring, to the fluid chamber 12a of the tube 12, which is in contact with the fingers, whereby the tube 14, which is not in contact with the fingers contracts, and the tube 12, that is in contact with the fingers expands.

Since the lengthwise expansion of the tube 12 is controlled by the core member 16, the tube 12 expands in the width direction while bending the core member 16, and the artificial fingers 8A and 8B are bent and deformed.

Then, the microcomputer 32 monitors the detection values of the pressure sensors 30, and determines that the greatly bent and deformed artificial fingers 8A and 8B has generated external force tending to open the O-ring when the pressure in the fluid chamber 12a increases rapidly. The microcomputer 32 starts to monitor the detection value from the contact-separation sensor 2, stores the gradually increasing pressure values of the pressure sensors 30 in the storage unit 32c, and continues to display the pressure values on the display 36.

When the microcomputer 32 confirms the separation of the thumb and the forefinger forming the O-ring by the detection value from the contact-separation sensor 2, the microcomputer 32 calculates a change in muscle strength of the voluntary muscles of the thumb and the forefinger of the examinee based on the storage table stored in the storage unit 32c and the pressure value, and displays the change on the display 36.

According to the O-ring test device constructed as described above, the pump sections 10 are controlled to bend and deform the artificial fingers 8A and 8B of the pair of artificial finger sections 4, the external force tending to open the O-ring is generated, and then the contact-separation state of the thumb and the forefinger is monitored by the contact-separation sensor 2, and the change in the voluntary muscles before and after the separation of the thumb and the forefinger can be calculated based on the output of the pressure sensors 30, and the change can be displayed on the display 36. Therefore, the results of the O-ring test can be obtained accurately only by the examiner.

In this embodiment, since an electric motor or the like, which is apt to generate electromagnetic waves, is not used, unlike in the conventional art, there is no external cause for exerting an influence on the vital reaction of the examinee, and the results of the O-ring test can be obtained more accurately.

In addition, since the core members 16 constituting the artificial fingers 8A and 8B maintain the parallel arrangement of the tubes 12 and 14 while flexing so that the lengthwise expansion of the tubes 12 and 14 is controlled and only the widthwise expansion is allowed, the artificial fingers 8A and 8B can be securely bent and deformed like human fingers.

In addition, since the tube 12 contacting the fingers of the examinee is formed of a flexible material, no uncomfortable sensation is given to the examinee who conducts the O-ring test.

In addition, since the covering member 18 is formed of a high polymer, the hydraulic oil is absorbed by the covering member 18 and does not leak to the outside even if the hydraulic oil leaks from the tubes 12 and 14.

Figure 4:
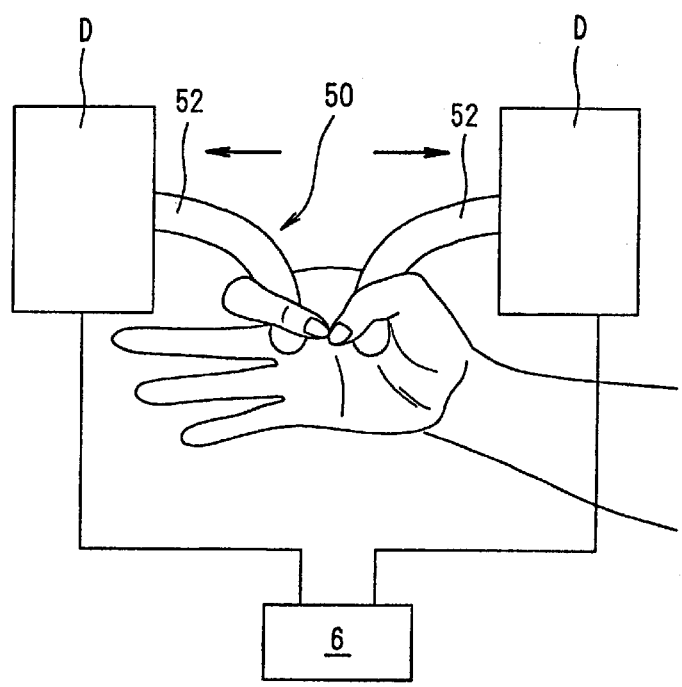
FIG. 4 is a view showing the general configuration of an O-ring test device in another embodiment in which the construction of an artificial finger is different.

In addition, since the pump sections 10 are integrally provided to the base ends of the artificial fingers 8A and 8B, and a large device, such as an electric motor, is not used, a compact configuration of the device can be achieved. FIG. 4 shows another embodiment of a pair of artificial finger sections.

Each of the pair of artificial finger sections 50 of this embodiment includes one artificial finger 52. The artificial finger 52 has the same construction as the artificial finger 8A of the first embodiment, and generates external force tending to open an O-ring by being bent and deformed.

When the pair of artificial finger sections 50 are controlled in a manner similar to the components of the first embodiment, similar action and effect can be obtained and one artificial finger 52 is controlled. Therefore, the control can be simplified.

As described above, the pump means is controlled to bend and deform at least two artificial fingers, the external force tending to open the O-ring is generated, and then the contact-separation state of the thumb and another finger is monitored by the contact-separation detecting means, and the muscle strength change-calculating means calculates the change in the muscle strength of the voluntary muscles before and after the separation of the thumb and another finger based on the detection value of the pressure detecting means. Therefore, the results of the O-ring test can be obtained accurately.

In addition, since the change in the muscle strength of the voluntary muscles calculated by the muscle strength change-calculating means can be seen by the display means, the results of the O-ring test can be obtained accurately only by the examiner.

In addition, a small pump part is integrally provided to the base ends of the artificial fingers, so that a compact configuration of the device can be achieved. Since an electric motor, which is apt to generate electromagnetic waves, is not used as the driving means, there is no external cause for exerting an influence on the vital reaction of the examinee, and the results of the O-ring test can be obtained more accurately.

In addition, since the core member maintains the parallel arrangement of the tubes while flexing so that the lengthwise expansion of the tubes is controlled and only the widthwise expansion is allowed, the artificial fingers can be securely bent and deformed like human fingers.

In addition, no uncomfortable sensation is given to the examiner who conducts the O-ring test.

Furthermore, even if the fluid leaks from the tubes, the fluid is absorbed by the outer periphery-covering member and does not leak to the outside.

What is claimed is:

1. An O-ring test device for testing an O-ring formed by a thumb and another finger consisting of voluntary muscles of an examinee, and for measuring body information according to a change in muscle strength of the voluntary muscles with external force tending to open the O-ring opposed against the muscle strength of the voluntary muscles of the examinee, the O-ring test device comprising:

at least two artificial fingers engaging with the thumb and another finger forming the O-ring, having at least two fluid-sealed fluid chambers arranged parallel to each other, and generating the external force tending to open the O-ring by being bent and deformed by the movement of the fluid between the fluid chambers;

a pump for moving the fluid between the plurality of fluid chambers;

a pressure detector for detecting pressure values in the artificial fingers when the external force is being generated;

a pump driver for controlling a drive of the pump;

a contact-separation detector for detecting contact-separation status of the thumb and another finger; and a muscle strength change-calculator for calculating a change in muscle strength of the voluntary muscles before and after the separation of the thumb and another finger detected by the contact-separation detector based on the output of the pressure detector.

2. An O-ring test device as claimed in claim 1, further comprising a display for displaying the result of the muscle strength change-calculator.

3. An O-ring test device as claimed in claim 1, wherein the pump is integrally connected to the base ends of the artificial fingers.

4. An O-ring test device as claimed in claim 3, wherein the pump includes a diaphragm defining a pump fluid chamber between the pump and ends of the artificial fingers;

a piezoelectric element stacked on the diaphragm; and a valve part for setting a direction of movement of the fluid between the fluid chambers of one finger.

5. An O-ring test device as claimed in claim 1, wherein the artificial fingers have a construction in which at least two slender tubes capable of expansion and contraction and having a fluid chamber accommodating therein a fluid are arranged in parallel to each other, and a flexible core member for controlling the lengthwise expansion of the tubes is provided between the tubes.

6. An O-ring test device as claimed in claim 5, wherein the tubes of the artificial fingers contacting the thumb and another finger forming the O-ring are formed of flexible elastic materials.

7. An O-ring test device as claimed claim 1, wherein the fluid sealed in the fluid chambers is liquid, and the outer periphery of the artificial fingers is covered by an outer periphery-covering member having a liquid absorption function.

8. A test device for testing an O-ring formed by a thumb and a finger of an examinee comprising:

at least two artificial fingers engaging with the thumb and the finger forming the O-ring;

each of said artificial fingers having at least two tubes disposed therein;

a pump fluidly communicating with said tubes;

a pressure sensor coupled to said artificial fingers for sensing pressure values in said artificial fingers;

a contact-separation sensor adjacent said thumb and said finger for detecting a contact-separation status of said thumb and said finger; and a muscle strength change-sensor coupled to said examinee and said contact-separation sensor for calculating a change in muscle strength of said examinee before and after separation of said thumb and said finger detected by said contact-separation sensor.

9. The test device of claim 8, wherein said pump includes a diaphragm defining a pump fluid chamber between the pump and ends of the artificial fingers; and a piezoelectric element stacked on the diaphragm.

10. The test device of claim 9, wherein said pump includes a valve part for setting a direction of movement of said fluid between said fluid chambers of said finger.

11. The test device of claim 8, wherein said tubes further comprise expandable and contractable members including a fluid chamber therein accommodating a fluid.

12. The test device of claim 10, wherein a flexible core member is disposed between said tubes for controlling a lengthwise expansion of said tubes.

13. The test device of claim 11, wherein the tubes of the artificial fingers contacting the thumb and the finger forming the O-ring are formed of flexible elastic material.

14. The test device of claim 8, wherein an outer periphery of the artificial fingers is covered by a liquid absorbing member.

15. The test device of claim 8, wherein said tubes are arranged parallel to each other.

16. The test device of claim 15, wherein said tubes contain a plurality of fluid chambers.

17. The test device of claim 8, wherein said muscle strength change-sensor calculation is based on an output of said pressure sensor.

* * * * *

UNITED STATES PATENT AND TRADEMARK OFFICE
CERTIFICATE OF CORRECTION

PATENT NO. : 6,389,907 B2
DATED : May 21, 2002
INVENTOR(S) : Yo Shishihara, Kunihiko Takagi, Takeshi Seto, Satoshi Kinoshita and Yoshinori Awanohara It is certified that error appears in the above-identified patent and that said Letters Patent is hereby corrected as shown below:

<u>Title page,</u>
Item [57], ABSTRACT,
Line 1, delete "generates" and insert -- means for generating --
Line 3, "examiner and" should be -- examinee is --

Signed and Sealed this

Eighth Day of October, 2002

*Attest:*

*Attesting Officer*

JAMES E. ROGAN
*Director of the United States Patent and Trademark Office*